(12) United States Patent
Nüsser et al.

(10) Patent No.: US 9,364,594 B2
(45) Date of Patent: Jun. 14, 2016

(54) BLOOD PUMP (75) Inventors: Peter Nüsser, Kleinmachnow (DE); Georg Konstas, Igersheim (DE)

(73) Assignee: Berlin Heart GmbH, Berlin (DE)

( * ) Notice: Subject to any disclaimer, the term of this patent is extended or adjusted under 35 U.S.C. 154(b) by 130 days.

(21) Appl. No.: 14/115,460

(22) PCT Filed: May 4, 2012

(86) PCT No.: PCT/EP2012/002009
§ 371 (c)(1),
(2), (4) Date: Feb. 27, 2014

(87) PCT Pub. No.: WO2012/150045
PCT Pub. Date: Nov. 8, 2012

(65) Prior Publication Data
US 2014/0171727 A1 Jun. 19, 2014

Related U.S. Application Data

(60) Provisional application No. 61/482,811, filed on May 5, 2011.

(30) Foreign Application Priority Data

May 5, 2011 (EP) .................................... 11075080

(51) Int. Cl.
*A61M 1/10* (2006.01)
*A61M 1/12* (2006.01)

(52) U.S. Cl.
CPC ............. *A61M 1/1015* (2014.02); *A61M 1/101* (2013.01); *A61M 1/1017* (2014.02); *A61M 1/1029* (2014.02); *A61M 1/1086* (2013.01); *A61M 1/122* (2014.02)

(58) Field of Classification Search
CPC . A61M 1/122; A61M 1/1015; A61M 1/1086; A61M 1/1017; A61M 1/1029; A61M 1/101
USPC .............................................. 600/16
See application file for complete search history.

(56) References Cited

U.S. PATENT DOCUMENTS 5,575,630 A * 11/1996 Nakazawa ............ A61M 1/101
  415/900
6,093,001 A * 7/2000 Burgreen .............. A61M 1/101
  415/176

(Continued)

FOREIGN PATENT DOCUMENTS

DE 10108810 8/2002
WO WO98/41759 9/1998

(Continued)

*Primary Examiner* — Carl H Layno
*Assistant Examiner* — Erin M Piateski
(74) *Attorney, Agent, or Firm* — Brinks Gilson & Lione (57) ABSTRACT

A blood pump having an axially tubular inlet, a tangential chamber adjoining the axial inlet and having a substantially radial outlet, with an axial guide body connected to the outlet and/or to the tangential chamber, an impeller supported on the guide body and having an inner surface facing the guide body and an outer surface as well as blading arranged on the outer surface. At least one part region of the guide body projects from the tangential chamber into the inlet, wherein at least one section of the stator transmitting a force onto the rotor is arranged in the part region. The impeller is supported by a hydrodynamic radial bearing in the radial direction.

23 Claims, 7 Drawing Sheets (56) References Cited

U.S. PATENT DOCUMENTS

| | | | | |
|---|---|---|---|---|
| 6,422,990 B1 * | 7/2002 | Prem | ............... | A61M 1/101 600/17 |
| 2001/0031210 A1 * | 10/2001 | Antaki et al. | ............... | 417/356 |
| 2003/0124007 A1 * | 7/2003 | Schima et al. | ............... | 417/420 |
| 2008/0262289 A1 | 10/2008 | Goldowsky | | |

FOREIGN PATENT DOCUMENTS

| | | |
|---|---|---|
| WO | WO98/50089 | 11/1998 |
| WO | WO01/70300 | 9/2001 |

* cited by examiner

BLOOD PUMP

CROSS-REFERENCE TO RELATED APPLICATIONS

This application is a 371 nationalization of PCT/EP2012/002009, which in turn claims benefit of European patent application 11075080.9 filed on May 5, 2011 and U.S. Provisional Application 61/482,811 filed on May 5, 2011.

BACKGROUND

The invention relates to the field of blood pumps.

Here and in the following, a blood pump is understood as a pump which serves the assistance or establishing of a flow of blood within a human or animal body and is suitable for implanting in the chest area of a human or animal outside the heart. With left ventricular blood pumps (left ventricular assist devices, LVADs), there is a connection between the left half of the heart and an inlet of the blood pump as well as between an outlet of the blood pump and the aorta branching from the heart to assist or establish the blood circulation through the body (systemic circulation). With right ventricular blood pumps (RVADs), there is a connection between the right half of the heart and the pulmonary trunk which leads to the left and right pulmonary arteries (or a direct connection between the RVAD and the left and/or right pulmonary artery/arteries) to assist or establish the blood circulation through the lung (pulmonary circulation). The blood is conducted within the blood pump through a hollow body which is part of a pump housing or is arranged in such a pump housing. A rotating impeller having blading for generating a pressure and a flow of the blood resulting therefrom is provided in the hollow body. So-called total artificial heart (TAH) pumps include left and right ventricular blood pumps to assist or establish the total blood circulation. Connections hoses and tubes as well as optionally flow manifolds are used to establish the named connections between the blood pump and the heart or the blood vessels. In addition, at least one cable harness is required for the energy supply and optionally for the control of the blood pump, said cable harness connecting the blood pump to an energy reservoir and optionally to a control unit. Alternatively, the pump can be transcutaneously supplied with energy.

One main problem in the implanting and use of such blood pumps is the space requirement of such blood pumps and of the connection hoses as well as the cable harness in the chest space close to the heart.

A further difficulty can be found in the risk of destruction of blood cells (hemolysis) by the blood pump, in particular at mechanical bearings of the impeller, in constrictions or abrupt changes in direction of the flow of blood through the blood pump and by high pressure gradients within the blood pump. In the design of blood pumps, mechanical bearings of the impeller are for this purpose frequently replaced with a magnetic and/or hydrodynamic bearing apparatus.

Numerous blood pumps are known in the prior art. A blood pump is disclosed in WO 2007/105842 A1 which includes an impeller having a rotor, wherein the impeller is placed onto a first conducting body in the manner of a sleeve. A rotor is understood here and in the following in each case as a motor rotor, i.e. a component of the motor which is stored in a cavity of the impeller in some embodiments and which is formed by a magnet. The pump moreover includes a guide wheel. With the help of magnetic bearings, the impeller is radially supported on the guide body and axially supported between the guide bodies.

A centrifugally operating pump is proposed in each of U.S. Pat. Nos. 6,015,272, 6,244,834, 6,447,265 and 6,447,266 which has a pump housing having a central spigot or pin. An impeller having a bore corresponding to the spigot moves on this spigot, with the outer shape of the impeller or its hub being conical. The blading of the impeller is attached to this conical outer surface and effects the primarily centrifugally operating pumping power. A blood gap in which a secondary flow path arises is formed between the inner cylindrical surface of the rotor and the spigot. Permanent magnets are used to support the impeller in the radial direction and actively regulated magnets to support the impeller in the axial direction. The fluid is expelled from the pump through a spiral outlet. U.S. Pat. No. 5,370,509 shows a blood pump, wherein the guide body tapers conically in the upstream direction and an impeller having a blading varying in the radial extent is formed on the conical guide body. A stator which is disposed within the guide body and which acts on a rotor arranged in the impeller is located in the proximity of the wall of the tangential chamber disposed downstream for driving the impeller. Due to the conical form, further magnets are used for the axial and radial support which are also arranged in the pump housing.

A further pump is shown in U.S. Pat. No. 5,211,546. It is in this respect an axially operating pump in which the impeller is placed onto a pin-like guide body in the manner of a sleeve. Furthermore, guide wheels which are connected via guide vanes to a wall of the tube surrounding the impeller are located upstream and downstream of the impeller. The guide wheels have magnetic bearings for the improved axial support of the impeller.

Although the initially named heart pumps are occasionally already in practical use, there is still the need for high-performance, space-saving pumps.

It is the object of the present invention to propose a blood pump which takes up the aforesaid problem and offers an improvement.

SUMMARY

A blood pump in accordance with the invention includes an axial, tubular inlet which is formed as a hollow body and at which a tangential chamber having a substantially radially outlet adjoins. Furthermore, a guide body is present which extends in the axial direction and which is connected either to the inlet and/or to the tangential chamber and is in this manner held substantially coaxially to the axial tubular inlet in the course of flow. An impeller having an inner surface facing the guide body and an outer surface remote from the guide body is supported on the guide body. The impeller moreover has blading arranged on its outer surface so that blood flowing through the tubular inlet is transported axially in the direction of the tangential chamber and is conveyed within the tangential chamber to the radial outlet.

Furthermore, the blood pump includes a stator associated with the guide body and a rotor associated with the impeller by which the rotation of the impeller arranged on the guide body is effected.

In accordance with the invention, at least one part region of the guide body projects from the tangential chamber into the inlet. Since the part region also projects into the tubular inlet, a reduction in size of the tangential chamber is possible and parts or sections of the impeller and of the blading arranged on the impeller can be transposed into the axial tubular inlet. In this manner, the blood pump can be shortened in its axial length since the impeller no longer has to be completely held within the tangential chamber or spiral chamber.

Furthermore, at least one section of the stator transmitting force onto the rotor is located in this part region so that the tangential chamber can furthermore be made in shortened form. Since parts of the stator no longer have to be stored in the tangential chamber, the comparatively large outer radius of the spiral chamber or tangential chamber of the pumps known from the prior art can be reduced since parts of the driving component of the motor are transposed into the part region of the guide body. Furthermore, a taring of the impeller on the guide body is considerably simplified due to this arrangement. Since a section of the impeller is preferably arranged on the guide body such that the rotor arranged in the impeller can be driven by the force-transmitting section of the stator in the part region of the guide body, and in particular for the case that the rotor is arranged in section of the impeller at the middle from an axial aspect, less torques generating imbalance are transmitted from the stator onto the rotor. In particular the radial and axial support of the impeller on the guide body is hereby substantially simplified.

Since the impeller is supported in a radial direction in accordance with the invention by a hydrodynamic radial bearing, a substantial design simplification over the prior art is made possible in the interaction of the arrangement of the part region, of the force-transmitting section of the stator and of the hydrodynamic radial bearing. Due to the cooperation of the aforesaid three features, it is in particular possible not to arrange any further drive components radially outside the blading of the impeller, i.e. in particular not to arrange any further drive components on an outer surface of the axial tubular inlet or on an outer surface of the tangential chamber. Furthermore, drive components or support components arranged axially, i.e. downstream, of the tangential chamber are not necessary and can be dispensed with. In this manner, the blood pump can be manufactured in a particularly small construction shape so that the implanting of the blood pump is simplified. Normally, the pump operation is set such that the pressure at the radial outlet is greater than at the axial inlet.

An omission of a guide wheel disposed upstream of the impeller is furthermore possible in accordance with the invention. In this case, the guide body is, for example, formed as a pin which projects from the tangential chamber into the outlet and on which the impeller is plugged. The putting together of the different components of the blood pump is therefore also hereby simplified, whereby errors in the assembly can be further avoided and the quality management of the blood pump is simplified.

In a further embodiment, the impeller is radially supported in the radial direction only by a hydrodynamic radial bearing preferably formed between the inner surface of the impeller and a guide body outer surface.

The number of the required components for producing the blood pump is further reduced by the design of the radial bearing only as a hydrodynamic bearing. Additional space in the guide body is moreover released (since no radial support magnets are required) which can in turn be made available to the force-transmitting components of the stator. The torque which can be generated by the stator can hereby be increased due to the larger dimensioning of the stator elements.

In a further embodiment, the hydrodynamic radial bearing is formed by cut-outs on a guide body outer surface and/or on the inner surface of the impeller. The hydrodynamic radial bearing can be adapted to the performance spectrum of the blood pump by corresponding passages of the inner surface of the impeller or of the guide body outer surface. The gap widths between the guide body outer surface and the inner surface of the impeller can be selected, for example, between 20 μm and 200 μm. The cut-outs or passages of the surface extend, for example, from 1 mm to 20 mm in the axial direction. The performance spectrum of the blood pump is to be understood in this respect as the desired blood conveying amount, the revolutions required for this (2000 r.p.m. to 3500 r.p.m.) of the blood pump and the blood pressure hereby to be produced. The performance spectrum is selected in this respect such that the pump is suitable for setting very different values of the blood pressure within a range from approximately 5 mmHg to approximately 150 mmHg within a stable, constant volume flow adapted to the physiological conditions between 0 l/min and 20 l/min and can be used in this manner both as an RVAD and as an LVAD and is suitable for the construction of a total heart pump, for instance.

In a further embodiment, the hydrodynamic radial bearing is designed such that it includes two or more pairs of inner surface sections of the impeller and of respective guide body outer surface sections corresponding thereto. This in particular means that, for example, that section of the guide body in which the force-transmitting components of the stator are disposed has a diameter which is larger or smaller with respect to the remaining guide body outer surface sections covered by the impeller. A further improvement of the hydrodynamic support is hereby given, with it being adapted to the desired performance spectrum.

In a further embodiment, the impeller and the guide body are formed is such a manner or have additional components by which in the axial direction, i.e. in the direction of the axis of the guide body and the axis of the impeller extending coaxially thereto, a preferably passive magnetic axial bearing is provided for the axial support. To hold the impeller on the guide body, either an active magnetic control can be used for the axial positioning or a passive axial bearing can be used, for example formed by permanent magnets. Alternatively to the axial support by the permanent magnets which have to be stored both in the guide body and in the impeller, the axial magnetic bearing can also be formed by the interaction of the stator and the rotor since the magnetic field also includes axial components between the rotor and the stator. The magnetic field in particular also acts in an axially centering manner between the yoke (for example, the stack of sheets) of the stator and the permanent magnet of the rotor. In this respect, the axial component of the magnetic field of the motor is set so that the axial force generated by the motor counters the force generated by the onflowing fluid or the axially centering component of the motor magnetic field is larger. Since additional permanent magnets or actively regulated magnets are not required for the axial support in this variant, more construction space for the motor can be provided or construction space can be saved and the pump can be reduced in size.

It is advantageous on the use of an axial bearing on the basis of permanent magnets, in particular for utilizing the construction space within the guide body or the impeller for the motor components, to arrange the components of the axial bearing which may be necessary downstream or upstream of the rotor or of the elements of the stator transmitting the force. Preferably, the components for the axial support should in particular be arranged at the end of the impeller disposed upstream and the section of the guide body corresponding thereto as well as on the side of the impeller disposed downstream and the side of the guide body corresponding thereto arranged downstream. A stable axial support can hereby already be achieved with relatively weak magnetic fields. In accordance with the prior art, the magnets are magnetized for the axial support coaxially to the axis of the guide body or of the guide body outer surface or the impeller inner surface.

To allow a simplified manufacture of the blood pump, the guide body can have a hollow space in which the stator and the force-transmitting components of the stator are arranged. Furthermore, further hollow spaces, for example for components of the axial support, can be provided or a single hollow space can be present in which all bearing and stator components are arranged. The manufacture of the blood pump is hereby considerably simplified.

In a further embodiment, the guide body is connected to a wall of the tangential chamber disposed downstream. The guide body hereby projects as a spigot through the tangential chamber into the tubular inlet and no further guide wheels are required. The advantage in particular results from this that the cable harness which has to be guided into the guide body inter alia for the power supply of the stator is guided directly into the guide body through the wall of the tangential chamber disposed downstream. In particular no complex and/or expensive designs are required here for leading cables through guide wheel blades supported at the inlet or at side walls of the tangential chamber.

A cavity of a tangential chamber preferably has an axial extent with respect to an impeller in a ratio of 1:2 to 1:7, preferably from 1:3 to 1:4.5, i.e. the impeller is longer than the axial extent of the cavity.

In a further embodiment, the stator is formed by windings, coils or similar. The windings can in this respect be suitable coils generating a high magnetic field density. Both distributed windings and tooth coils of any desired number of phases are suitable. Further suitable coil geometries result from the prior art for the skilled person.

In order additionally to increase the magnetic field strength and thus to ensure an improved force transmission, provision can be made to design individual windings or all windings around preferably one or more ferrite cores in order additionally to utilize the magnetic field induced in the ferrite cores for the drive of the rotor. Corresponding arrangements for the design of a stator are sufficiently well known in the prior art.

In a further embodiment, the impeller is made in cylinder jacket form in at least the part section of the guide body which projects into the axial tubular inlet. The impeller is preferably not only made in cylinder jacket form in this part section, but rather over the entire length. A cylinder jacket is in this respect in particular substantially to be understood as a straight tube whose axis of symmetry is formed coaxially to the axis of the guide body.

The impeller preferably includes a hollow space, with the rotor or the elements forming the rotor being arranged in this hollow space. Alternatively to this, the components forming the rotor can be molded with a material forming the impeller.

The rotor is preferably formed (preferably in substantially circular form) by at least one alternatingly magnetized permanent magnet ring, but can include further such permanent magnet rings. Further components for forming the rotor can also be provided. The alternating magnetization is here to be understood as magnetization processes directed radially or diametrically toward the axis of the guide body in the part section or directed radially or diametrically away from the axis of the part section. For example, a permanent magnet segment is thus provided in a bipolar motor with a magnetization directed radially or diametrically away from the axis and a permanent magnet segment with a magnetization directed toward the axis. To increase the power transmission, a number of such permanent magnet rings can be arranged viewed in an axial direction; however, a single permanent magnetic ring is preferred having an axial extent extending over the axial extent of the stator.

In an embodiment, a permanent magnet ring is formed by a one-piece ring magnet or from a plurality of respective individually magnetized part segments. A ring magnet is in this respect understood as a one-piece ring of a magnetic material which is first formed as a ring and which is subsequently magnetized, i.e. different sections of the ring are subsequently magnetized.

If the permanent magnet ring is composed of a plurality of segments, i.e. more than two segments, every single segment can first be magnetized and the segments can subsequently be assembled to a ring. In this respect, adjacent segments are each alternatingly magnetized. The individual segments can in this respect either contact one another or adjacent segments can be spaced apart from one another by spacers. Spacers can in this respect be produced from paramagnetic materials, for example.

In a further embodiment, the impeller is arranged on the guide body such that the blading of the impeller lies both within the tangential chamber and in the inlet. It is hereby possible to ensure the axial conveying of the blood through the tubular inlet and thus to ensure a particularly blood-saving conveying of the blood into the radial chamber or tangential chamber or spiral chamber. A helical chamber is also possible. While the chamber widens radially from a tongue toward the outlet with a spiral chamber, i.e. the volume of the chamber per angular segment increases due to the radial widening, the volume of the chamber per angular segment also increases in the axial direction with the helical chamber. A chamber can naturally also be selected having a radial outlet whose volume per angular segment (viewed from a tongue) increases both in the radial direction and in the axial direction and thus forms a combination of spiral chamber and helical chamber. The term tangential chamber in this application covers both spiral chambers and helical chambers and their combinations.

Only after the blood has been given an axial advance does it move into the tangential chamber from which there is only one single radial outlet (optionally a plurality of outlets are also conceivable) so that the blood-saving axial conveying is combined with the space-saving radial outlet.

The tangential chamber preferably has at least one tongue, but can also include a plurality of tongues. The number of tongues can in particular correspond to the number of blades of the impeller to ensure a particularly efficient and gentle conveying of the fluid. Such a tangential chamber is called a double spiral chamber or a multispiral chamber, for example.

In a further embodiment, the blading is formed as a helix arranged on the outer surface. The helical blading is made as single start or multistart to achieve the axial propulsion of the blood. The helix can therefore have one or more, preferably two to six, helical blades which each run around the impeller partly, completely or in multiple form with respect to the axis of rotation. The blades include a non-vanishing angle of engagement with the axis of the impeller and the conveying effect of the impeller can be set via it.

On a rotation of the impeller about the axis, the helix transmits an axially aligned force to volume portions of the blood adjacent to the blades. In this manner, the blood is "pushed" through the tubular inlet by means of the helix. The transmission of the axial propulsion onto the blood by means of the helix has proved to be particularly gentle on the blood in this respect. In contrast to this, the rotor blades of radial flow pumps are generally aligned parallel to the axis of rotation of the impeller or only have a small angle of engagement. The rotor blades of the radial flow pumps predominantly transmit a tangentially aligned force; however, lower axial forces to the volume portions of the blood adjacent to the rotor blades. The volume portions adjacent to the rotor blades are thus set into a rotational movement about the axis of rotation of the impeller in radial flow pumps so that the blood is accelerated radially outwardly via centrifugal forces and is conveyed out of the pump through the outlet. The blood receives an axial propulsion in radial flow pumps, which are also called centrifugal pumps, only by an axial suction effect which is caused by the outflow of the blood out of the pump. In contrast, in the pump in accordance with the invention, the blood is "pushed" by the helix at least partly in the axial direction within the pump.

The helix is preferably designed as continuous. The helix preferably extends over at least 80% of the axial extent (length) of the impeller, particularly preferably over at least 90% of the axial extent of the impeller. Provision can, however, also be made that the helix extends over the total length of the impeller. In this manner, the impeller is suitable for a particularly gentle and low-eddy axial propulsion of the blood. In addition, the conveying effect of the helix can be modified particularly easily by a variation of the angle of engagement of the helix and/or of a local gradient of the helix K. The local gradient K of the helix, measured at a predefined axial height of the helix, is in this respect defined as usual as the ratio of an axial displacement of an infinitesimally small volume element $\Delta X$ adjacent to the helix at the named height of the helix, which is caused by a rotation of the impeller by an infinitesimally small angle of rotation $\Delta\phi$, divided by the angle of rotation $\Delta\phi$, that is $K=\Delta X/\Delta\phi$. A local pitch H of the helix thus results as an axial displacement of a volume element adjacent to the helix by the helix, measured at a predefined axial height of the helix which is caused by a complete rotation of the impeller, that is $H=2\pi K$.

The local pitch of the helix over the total axial extent of the helix preferably lies in a range between approximately 0.5 mm and 20 mm. This corresponds to a local pitch between approximately 3 mm and 130 mm. Provision is made in a further development that the local gradient of the helix at an inflow side of the impeller, i.e. disposed upstream, lies between 0.5 mm and 2 mm. This corresponds to a local pitch between approximately 3 mm and 13 mm. The local gradient at a flow-off side of the impeller amounts to between 3 mm and 20 mm. This corresponds to a local pitch between approximately 18 mm and 130 mm. Provision can moreover be made that the local gradient and the local pitch of the helix increase constantly toward the flow-off side of the impeller.

The average of the local gradient over the total axial extent of the helix is defined as the mean gradient. Analog to this, the average of the local pitch over the total axial extent of the helix is defined as the mean pitch of the helix. In a preferred embodiment, the mean gradient is between 1 mm and 5 mm; this corresponds approximately to a mean pitch of approximately 6 mm or approximately 30 mm.

In principle, a larger gradient, or a smaller angle of engagement, results in a higher transmission of swirl onto the blood. In addition to the axial "pushing forward" of the blood by the helix, the application of swirl (rotational energy) to the blood is used for building up pressure in accordance with the invention. Provision is therefore made in the embodiments that the helix extends up to and into the tangential chamber of the blood pump. Since the blood flows out tangentially vial the outlet out of this tangential chamber, the rotational energy of the blood is thus also used efficiently for the pressure build-up in addition to the axial flow energy of the blood.

An outer contour of the helix is preferably designed substantially as cylindrical, i.e. the radial maximum extent of the helix remains constant over this length. Equally, the jacket surface of the impeller which carries the helix can also be designed substantially as cylindrical. Furthermore, the impeller is preferably elongated in the axial direction and has a maximum diameter which is preferably not larger than 50% of the axial extent of the blading of the impeller, particularly preferably not larger than 30% of the axial extent of the impeller. A particularly slim construction shape of the blood pump can be achieved by an elongated shape of the impeller. Furthermore, in this manner, a particularly long axial extend of the helical blading of the impeller can be achieved for a particularly uniform and blood-saving axial conveying of the blood.

Provision is made in a further development that a maximum radial extent of the blading, that is the maximum height of the blading, is less than 50% of a maximum total radius of the impeller (measured perpendicular to the axis of rotation and including the blading), preferably less than 30% of the maximum total radius. The maximum height of the blading is typically in a range between 1 mm and 4 mm, particularly preferably in a range between 2 mm and 3 mm.

Provision can also be made that the blading is given by at least one blade, with the at least one blade having a maximum thickness (measured perpendicular to the axis of rotation and perpendicular to the height of the blading) which is less than 10% of a maximum total extent of the impeller (measured perpendicular to the axis of rotation and including the blading); the maximum thickness of the blade preferably amounts to less than 5% of the maximum total extent. The maximum thickness is typically in a range between 0.5 mm and 3 mm, particularly preferably in a range between 1 mm and 2 mm.

Provision is made in a further embodiment that the inner surface of the impeller is a cylindrical inner surface and/or the outer surface of the impeller is likewise a cylindrical surface on which the blading is arranged.

Provision is made in this respect that the impeller has a maximum diameter which is not larger than 50% of an axial extent of the blading. A gentle energy transmission onto the blood is hereby realized.

In a further embodiment, the maximum radial extent of the blading is less than 50% of a maximum total radius of the impeller, including the blading. In this respect, the blading is measured from the outer surface of the impeller up to its radial margin.

In a further embodiment, the blading is given by at least one blade, with the at least one blade having a maximum thickness which is less than 10% of a maximum total extent of the impeller. In this respect, the blade can also designate a helical section.

Good conveying conditions for blood are hereby ensured and friction losses in the pump are minimized.

The radius of the impeller, including blading, preferably amounts to less than 100% of the inner diameter of the tubular inlet, but more than 90% of the inner diameter in order thus to prevent backflows of blood through a backflow passage formed between the inner diameter of the inlet and the outer diameter of the blading. This backflow passage preferably does not contribute substantially or significantly to the hydrodynamic support, but can optionally be used as a damping member.

Further combinations of blood pumps result from the further aspects of the invention. A variant is in particular provided in which the blood pump admittedly does not necessarily have a hydrodynamic radial bearing, but at least a part region of the guide body still projects into the inlet and at least one section of the stator transmitting force onto the rotor is arranged in this part region. Since the impeller can also be stored at its outer radial diameter through the gap between the inner diameter of the inlet and the outer diameter of the impeller, constructions without a purely hydrodynamic radial bearing are covered by the invention. It is in particular a further variant of the invention that a pump is formed without a radial hydrodynamic bearing or can have further bearings, but a part region of the guide body still projects into the inlet and the guide body in the part region includes a cylindrical guide body outer surface on which the impeller is formed as a cylindrical jacket at least in the part section. Numerous advantages of the invention can already be realized by these embodiments.

It must generally be mentioned that a smaller dimensioning with respect to commercial blood pumps is possible using a pump in accordance with one of the independent claims. Since the stator is arranged disposed inwardly in the guide body and the impeller including the rotor is supported on the guide body, neither the axial tubular inlet nor the tangential chamber or spiral chamber have to take up any further components of the motor or the bearing. It hereby becomes possible to form the walls of the inlet and of the tangential chamber particularly thin with respect to conventional models.

BRIEF DESCRIPTION OF THE DRAWINGS

Further embodiments will be made obvious to the skilled person by the following embodiments. It is pointed out that the features of the different embodiments can be combined with one another and that not all features of an embodiment are necessary to combine the respective embodiment with another embodiment. There are shown FIG. 1 a longitudinal section through a variant of a pump in accordance with the invention.

DESCRIPTION OF PREFERRED EMBODIMENTS

Figure 1:
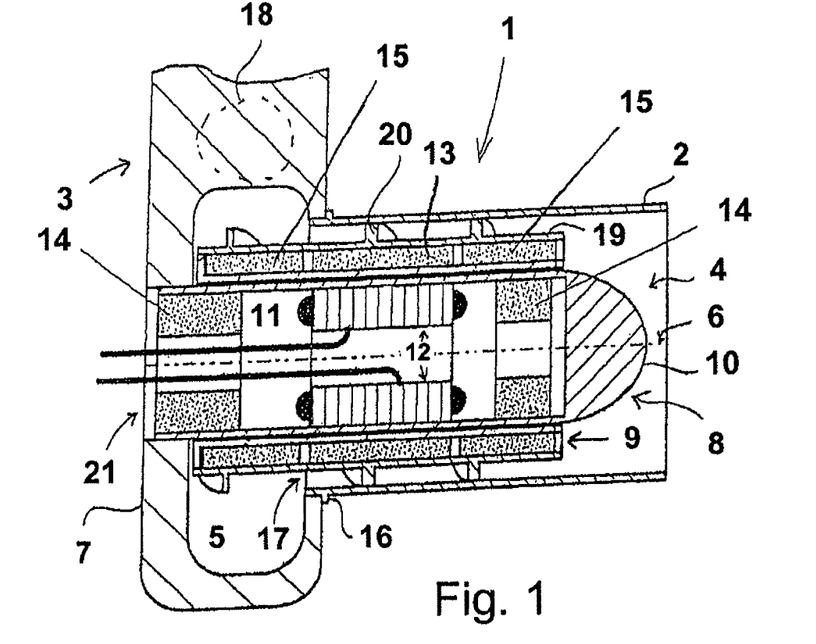

A pump 1 in a longitudinal section is shown in FIG. 1. The pump includes a tube 2 which forms the axial tubular inlet of the blood pump. The tube 2 is connected downstream to the helical chamber 3. The hollow space 4 of the tube 2 in this respect extends into the cavity 5 of the spiral chamber which opens into an outlet 18 not shown in any more detail in FIG. 1. In this respect, the axis 6 of the tube 2 and an axis of the outlet include an angle of 90°. In principle, however, angles between 45° and 135° are also possible. A guide body 8 which extends through the cavity 5 into the hollow space 4 of the tube 2 is arranged at the rear wall 7 of the spiral chamber.

The guide body 8 extends like a spigot into the hollow space 4, with the guide body 8 substantially having the form—with the exception of the cap 10 not covered by the impeller 9—of a cylinder jacket in which a hollow space 11 is arranged. The stator 12 of the motor of the blood pump which is operatively connected to the rotor 13 of the impeller 9 and effects a rotation of the impeller 9 is located in the hollow space 11. Permanent magnet systems 14 which have a magnetization parallel to the axis 6 are arranged in the hollow space 11. The permanent magnet systems 14 form, together with the permanent magnet systems 15 arranged in the impeller 9, a passive axial bearing which prevents an axial offset of the impeller 9 on the guide body 8.

To establish a connection of exact fit between the tube 2 and the spiral chamber 3, the tube 2 has a collar 16, with the diameter of the collar 16 being larger than the diameter of the opening 17 of the spiral chamber so that the tube cannot be pushed down to any depth into the spiral chamber, but the collar 16 rather forms a stop on the outer side of the spiral chamber 3. A permanent connection between the tube 2 and the spiral chamber 3 can take place, for example, via a thread, by welding or by adhesive bonding of the two aforesaid elements. Although the tube 2 and the spiral chamber 3 are prefabricated in the embodiment shown here as two mutually separate parts which are only subsequently connected, it is equally possible to connect an inlet having material continuity to the spiral chamber 3 so that the function of the tube 2 is effected by the inlet connected with material continuity to the spiral chamber 3.

Further details will be looked at in more detail in the following Figures.

Figure 2:
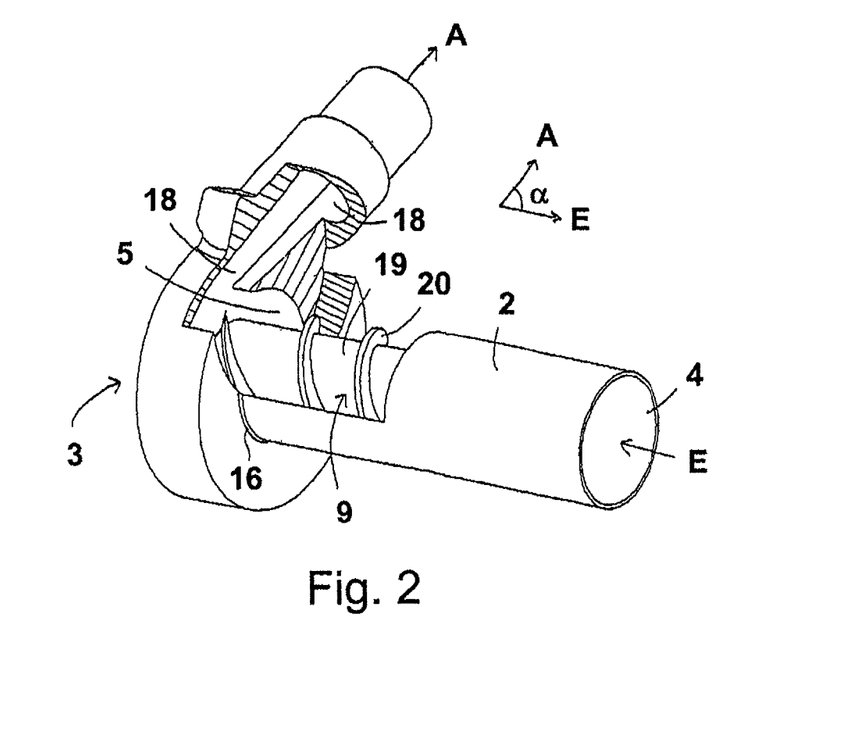
FIG. 2 a perspective view of the pump of FIG. 1.

A perspective view of the pump of FIG. 1 is shown in FIG. 2. The pipe 2 can be clearly recognized, as can the collar 16 by which the end of the tube 2 disposed downstream is supported on a wall of the spiral chamber 3 disposed upstream. In the present example, the outer diameter of the tube 2 is selected so that it fits into the inner diameter of the opening 17 of the spiral chamber 3 with an exact fit.

In FIG. 2, a part region of the wall, of both the tube and the spiral chamber 3, has been omitted for a clear representation so that the impeller 9 extending through the tube 2 into the cavity 5 of the spiral chamber 3 and the shape of the cavity 5 and its outlet 18 are illustrated. A blading 20 which is formed as a throughgoing helix in the present embodiment can be recognized on the impeller 9 beside the impeller outer surface 19. Reference is made to the general part of the description with respect to the possible embodiment of the helix.

With the aid of the blading 20 of the impeller 9, blood is pumped in the direction E from the tube 2 into the cavity 5 on the operation of the motor and is subsequently expelled through the outlet 18 in the direction A also due to the longitudinal component of the fluid speed. The angle $\alpha$ between the directions E and A in this respect amounts to $\alpha=90°$, but can also be varied in the interval $\alpha=45°$-$135°$. It can be clearly recognized in FIGS. 1 and 2 that no electrical drive or bearing components are arranged at the outer walls of the tube or of the spiral chamber, with the exception of the rear wall 7 of the spiral chamber (but indirectly via the guide body 8). All components of the stator and of the axial bearing are contained in the hollow space 11 of the guide body 8 and the spiral chamber 3 itself has no electrical components at all. This substantially contributes to the simplification of the structure.

Figure 3A:
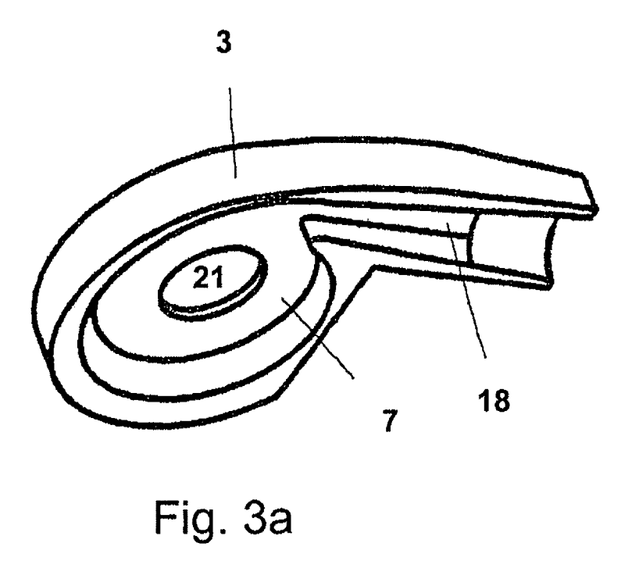
FIGS. 3a and 3b variants of a spiral chamber of the pump of FIG. 1.

A cross-section through the spiral chamber 3 is shown in FIG. 3a for a clearer illustration of the spiral chamber 3. The rear wall 7 includes an opening 21 having a diameter which is larger than the outer diameter of a guide body to be introduced. The radius of the opening 21 is preferably selected such that the inner side of the walls bounding the opening terminate with an exact fit with the outer diameter of any guide body. The radial outlet 18 is likewise clearly recognizable. The spiral chamber is preferably manufactured from a biocompatible material such as titanium, a ceramic material or coated plastics.

Figure 3B:
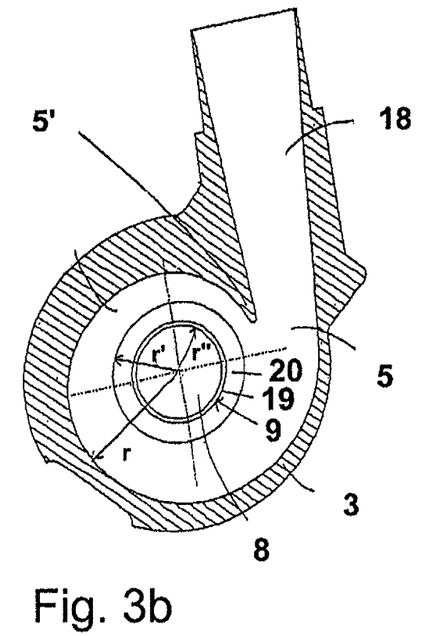

A perspective of the rear wall of the spiral chamber 3 different from FIG. 3a is shown in FIG. 3b. In this respect, a view from the tube 2 onto the spiral chamber 3 is shown. It can clearly be recognized that the radius r of the cavity 5 of the spiral chamber 3 increases anti-clockwise from the tongue 5'. The increase takes place up to the entry into the outlet 18. In addition to the spiral chamber 3, the guide body 8 is also shown which has an inner radius r''. Furthermore, the impeller 9 can be recognized, in particular the hollow space 36 receiving the rotor (see FIG. 5a) and the blading 19 which has an unchanging diameter of r'. The radius r' is selected such that a gap remains between an inner radius of the tube 2 and the outer radius r' of the blading 19. A particularly gentle manner of conveying of the blood is hereby made possible.

Figure 4:
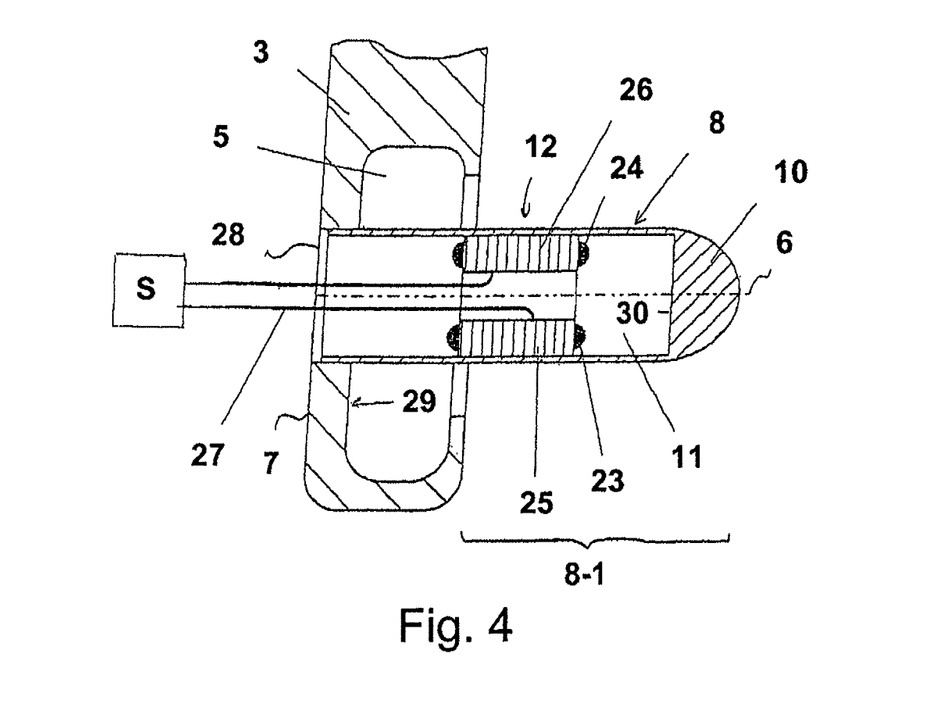
FIG. 4 a longitudinal section with a focus on a variant of the guide body.

In FIG. 4, both the spiral chamber 3 and the guide body 8 inserted into the rear wall 7 of the spiral chamber 3 are shown. It can clearly be recognized that a large part of the guide body 8, in particular the section 8.1, extends out of the spiral chamber and projects, as can be seen in FIG. 1, into the tube 2. The tip 10 of the guide body 8 is made in rounded form to bring about as gentle as possible an effect in the blood conveying.

The stator 12 which includes windings 23 and 24 which are arranged around a respective metal core 25 and 26 is located in the hollow space 11. The windings are wound of copper wire and are connected to the wiring 27 and can thus effect a movement of the impeller 9 arranged on the guide body 8. A control unit S, not explained in more detail, is provided for this purpose and effects the corresponding reversal of polarity of the magnetic field which is known from the prior art and which is generated by the windings 23 and 24.

The cavity 11 is closed by the tip 10, on the one hand, and by the cover 28, on the other hand. Only the wiring 27 projects out of the cover, all further stator components are located only in the hollow space 11.

It can furthermore be recognized that the ferrite cores 25, 26 of the stator 12 are arranged in the guide body 8 or in the hollow space 11 of the guide body 8 so that more than 90% of the volume of the parts of the stator transmitting the force, i.e. the ferrite cores or the windings, do not lie in the cavity 5 of the spiral chamber 3, but rather, as can be recognized in FIG. 1, project into the tube 2.

It can simultaneously be seen that the stator is arranged—apart from the wiring 27—approximately in the middle third of the guide body 8 (viewed in the axial direction, i.e. in the direction of the axis 6). The stator 12 is or the components of the stator 12 transmitting the force are arranged in the hollow space 11 such that the stator is also substantially arranged in the middle third of the hollow space from the inner side 29 of the rear wall 7 up to the end 30 of the hollow space 11 disposed upstream. The reason for this is a substantially symmetrical arrangement of the drive components. A symmetrical arrangement generally effects a symmetrical radial force distribution.

A stator arranged in the middle third thus effects a distribution of the radial forces between the rotor and the stator of the motor which is symmetrical with respect to the length of the impeller.

Although permanent magnets are drawn for the axial support in the variant of the pump of FIG. 1, these permanent magnets are not necessary if the axial support is effected by the stator and the rotor. The embodiment respectively shown in FIG. 4 (see also FIGS. 5a and 6) can thus also be made without permanent magnet systems 14 and 15 respectively.

In contrast to the variant shown in FIG. 4, it is naturally also possible to arrange an axial bearing in the middle third and to arrange the stator either in the front third or in the rear third of the guide body or both in the front third and in the rear third of the guide body 8. However, the wiring and the control of the windings hereby become more complex.

The impeller will be described in more detail in the following in FIGS. 5a and 5b. The impeller 9 is made up of an inwardly disposed cylinder 31 and an outwardly disposed cylinder 32, with the outer side of the outwardly disposed cylinder 32 forming the outer surface 33 and the inner side of the inwardly disposed cylinder 31 forming the inner surface 34. Both the inwardly disposed cylinder 31 and the outwardly disposed cylinder 32 have cylinder axes which lie coaxially to the drawn axis 6.

The inwardly disposed cylinder 31 has a collar, which has a width of r''', at its end 35 disposed downstream. This width is responsible for the volume of the hollow space 36 which is formed between the inwardly disposed cylinder and the outwardly disposed cylinder. The rotor 13 which is formed as a single permanent magnet ring 31 having four segments is located in this hollow space and the segments are polarized alternatingly directed diametrically outwardly or diametrically inwardly. The permanent magnet ring 37 contributes to the axial support of the impeller 9 on the guide body 8 in that the axial component of the magnetic field being formed between the rotor 13 and the stator counteracts an axial offset due to the fluid pressure difference present in the tangential chamber and the axial inlet.

On the manufacture of the impeller 9, first the rotor 13 is (and initially, if present, permanent magnetics 15) are pushed onto the inwardly disposed cylinder 31 and this combination is connected to the outwardly disposed cylinder 32 and is subsequently closed by a ring-like cover 38. Subsequently, the impeller 9 (or another variant of the impeller) is introduced into the tube 2 or the guide body is pushed into the opening of the impeller.

The position of the rotor 13 is selected in the present example such that the rotor 13 is substantially disposed axially directly opposite the stator 13 of the guide body 8. The force coupling between the rotor 13 and the stator 12 can hereby develop the best possible efficiency.

In the present example, this means that the rotor 13 is arranged in the impeller such that it lies completely within the hollow space 4 of the tube 2 when the impeller 9 is driven. Parts of the rotor can naturally, however, also be arranged in the hollow space 36 of the impeller 9 such that it extends at least partly into the cavity 5 of the spiral chamber 3.

Figure 5A:
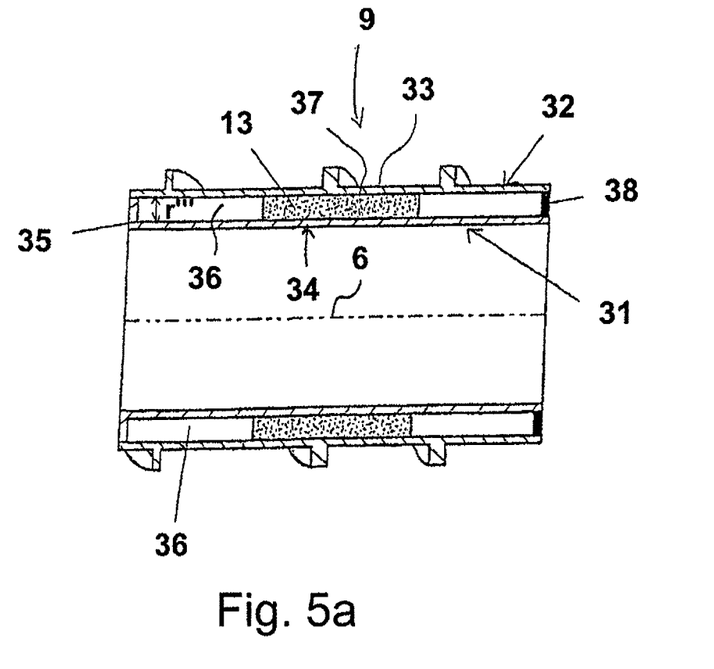
FIGS. 5a and 5b a longitudinal section and a cross-section through a variant of the impeller for a pump in accordance with the invention.
Figure 5B:
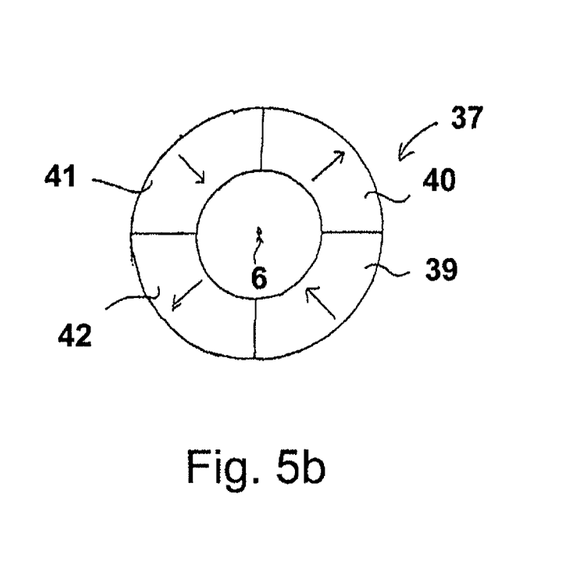

A cross-section of the rotor 13 is shown in FIG. 5b, with in particular a segmented permanent magnet ring 37 formed of individually magnetized segments being visible. The permanent magnet ring has alternatingly differently magnetized segments 39, 40, 41 and 42, with the segments 39 and 41 being polarized radially or diametrically inwardly and the sections 40 and 42 being polarized radially or diametrically outwardly.

A four-pole operation of the motor is possible using the permanent ring 37 shown here. The individual sections 39 to 42 each have an effective remanence of more than 0.5 T. To improve the coupling, segments having remanence values of more than 0.5 T, 1 T, 1.2 T or 1.4 T can generally be used.

Figure 6A:
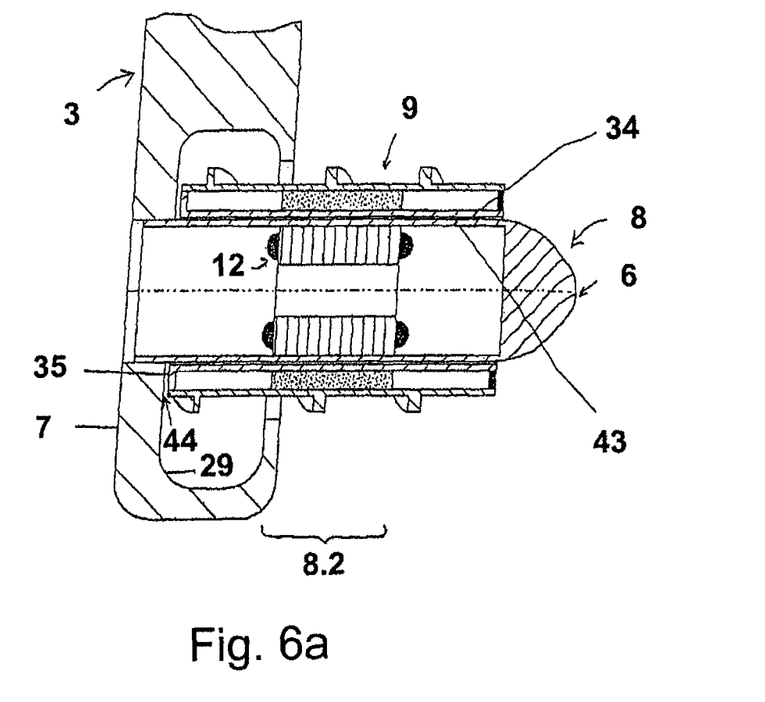
FIGS. 6a and 6b a longitudinal section through a further variant of a pump in accordance with the invention in a variant of an exclusively hydrodynamic radial bearing and of an axial bearing through the motor.
Figure 6B:
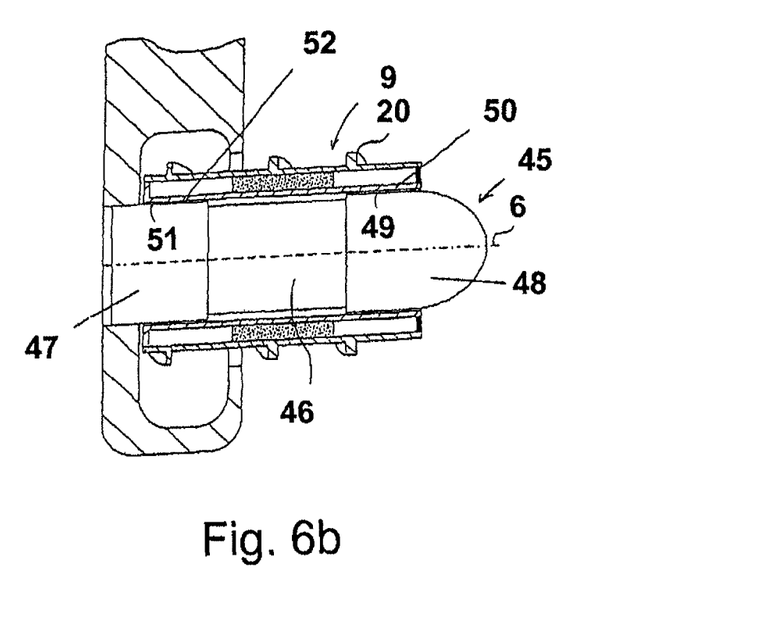

A further pump variant and generally the support of the impeller 9 on the guide body 8 will be looked at in more detail with reference to FIGS. 6a and 6b.

It can clearly be recognized that no additional axial bearing elements are provided in the pump variant of FIG. 6. The axial support is effected in this variant by the interaction between the stator and the rotor, with the axial component of the coupling magnetic field countering a force urging the impeller from the pin. This force substantially results from the passive axial centering effect of the permanent magnetic ring relative to the stator yoke. This force can be increased by suitable measures, e.g. inclination of the grooving of the stator or by an inclined polarization of the rotor. Except for the lack of axial bearing magnetics, the structure of the pump of FIG. 6 is substantially comparable with the pump structure of FIG. 1.

An outer surface 43 of the guide body 8 is separated by a gap having a radial width of some hundred micrometers from the inner surface 34 of the impeller 9. Both the surface 43 and the surface 34 can in this respect have cut-outs so that a hydrodynamic bearing is formed between the two surfaces when the impeller is set into rotation with the aid of the motor. Further radial bearings, for example magnetic radial bearings, are not provided; nor are further drive components or bearing components which are disposed radially outside the impeller.

It can be seen with respect to FIG. 5a that, in the case of a guide body 8 in the form of a cylinder jacket and in the case of an impeller 9 in the form of a cylinder, both elements can also be completely stored in a spiral chamber. For this purpose, for example, blading similar to the radial flow pumps can alternatively be provided. The advantage with respect to commercial models is that the force coupling between the impeller or the rotor of the impeller and the stator of the guide body is maximized due to the surfaces extending mutually in parallel and the support of the impeller is particularly simple. The costs for manufacturing a blood pump can hereby be substantially reduced. It is furthermore also possible to store, for example, an additional radial magnetic bearing in the guide body 8. This can in this respect completely or partly replace the bearing between the surfaces 34 and 43 which is formed as a purely hydrodynamic bearing.

It can be clearly recognized in FIG. 6a that the stator 12 is arranged in the part region 8.2 of the guide body 8, with more than 90% of the part region 8.2 being located outside the spiral chamber 3. Not only the gap between the surfaces 34 and 43 thus results in interaction with the tube 2, but also a gap between the radial margin of the blading 20 of the impeller 9 and of the inner wall of the tube 2. A damping member can hereby be provided on a corresponding dimensioning. In the present variant, the gap does not, however, essentially contribute to the hydrodynamic support.

A further variant of a purely hydrodynamic bearing can be seen from FIG. 6b. The guide body 45 has a smaller diameter in its middle section 46 with respect to the regions 47 and 48 at the margins. It is common to all three regions 46 to 48 that they are formed coaxially to the axis 6. A surface 49 of the section 48 of the guide body 45 covered by the impeller 9 forms, together with the oppositely disposed part 50 of the surface 34, a first section of a hydrodynamic radial bearing. Analogously to this, a further section of the hydrodynamic radial bearing is formed between the surface 51 of the section 47 and the part surface 52 disposed opposite this surface. The middle section 46 and the part surface 53 disposed opposite it can also be a part of the hydrodynamic radial bearing. In the present case, the part surface 53 and the middle section 46 are spaced apart from one another such that they do not contribute (or do not contribute significantly) to the hydrodynamic bearing since an uninterrupted radial bearing is admittedly stiffer, but energetically less favorable, in pump operation. The hydrodynamic radial bearing includes a plurality of cylinder surfaces which are adjacent to one another and which ensure the stable running of the impeller on the guide body 45.

Figure 7A:
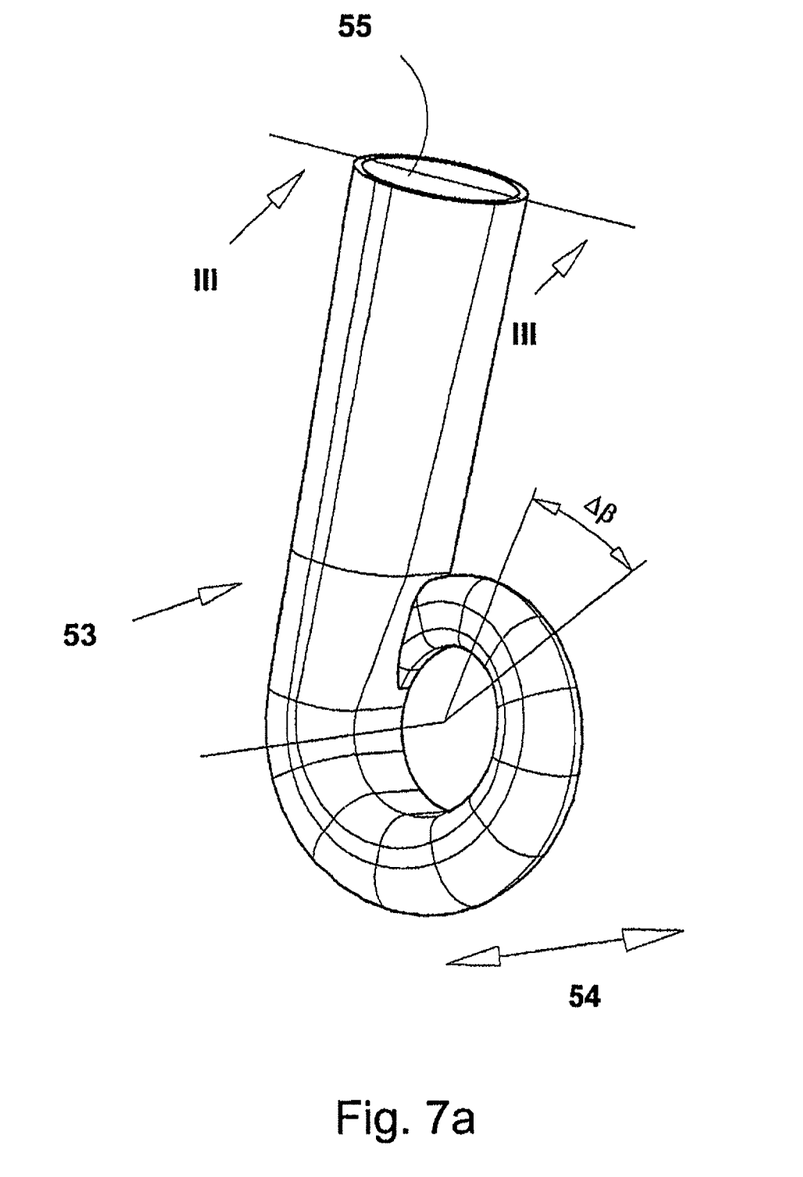
FIGS. 7a to 7c a variant of a helical chamber.
Figure 7B:
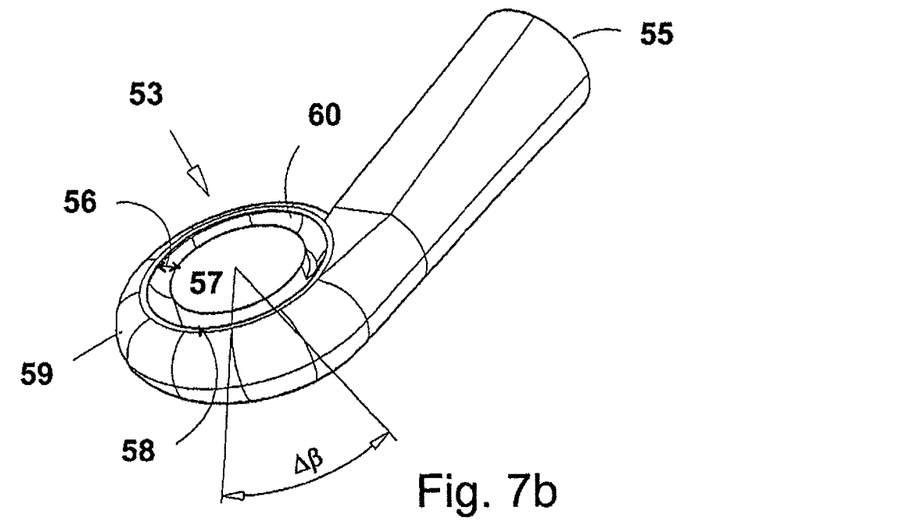

A helical chamber is shown by way of example in FIG. 7. The helical chamber 53 is shown from the rear side in FIG. 7a and from the front side in FIG. 7b along the section III of the helical chamber of FIG. 7a from the front side.

Figure 7C:
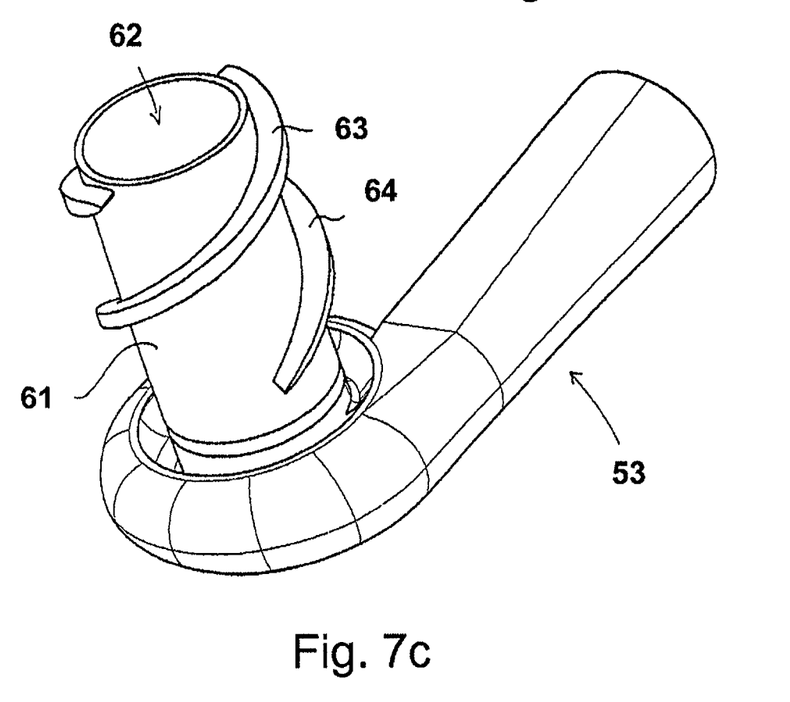

It can clearly be recognized in FIG. 7a that the axial extent 54 of the cavity or chamber of the helical chamber 53 increases continuously clockwise toward the radial outlet 55 per angular element As can be recognized with reference to FIG. 7b, the radial extent 56 does not increase between the solid plate 57 and the margin 58 outwardly bounding the helical chamber 53, but rather remains constant. Only the axial extent of the cavity 59 varies from the tongue 60 in FIG. 7b running counter-clockwise per angular element $\Delta\mu$. A particularly gentle blood conveying is possible with the helical chamber 53. A spigot for receiving the impeller is arranged on the plate 57. This is illustrated in FIG. 7c in which the impeller 61 is pushed onto a pin or spigot 62, with the pin 62 being installed on the plate 57. It can moreover be recognized that the blading formed as a helix has two blades 63, 64 with pitches varying in the axial direction. A cap such as in FIG. 1 is not, or not yet, placed onto the pin.

Figure 8:
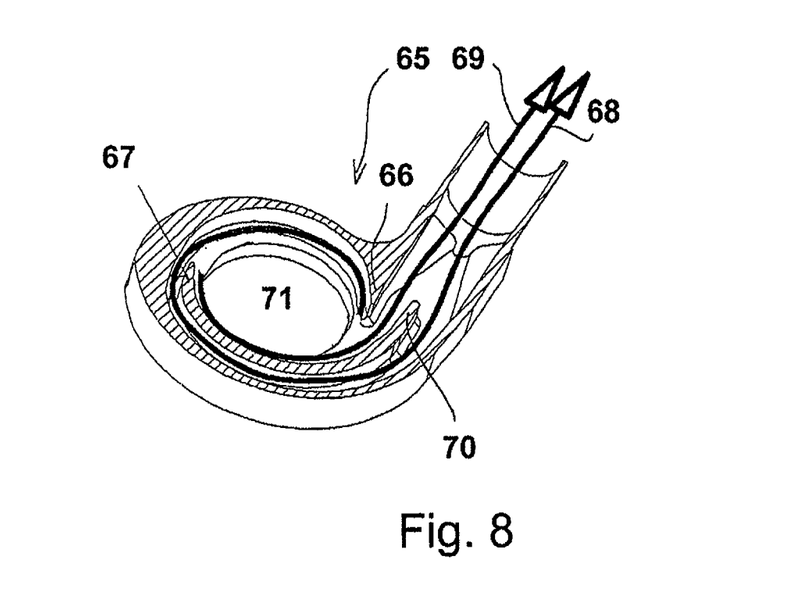
FIG. 8 a variant of a double spiral chamber.

In FIG. 8, a cross-section of a variant of a double spiral chamber is shown which can be used as a tangential chamber of a pump in accordance with the invention, of a pump with an outwardly disposed stator, as shown in PCT/EP2010/006863 or U.S. 61/258,932, or as an independent invention (this also applies to an N-fold chamber described in the following). The double spiral chamber 65 includes two tongues 66, 67 which effect two flow paths 68 and 69 respectively. The flow paths open into one another at the end 70 of the tongue 67 and strive out of the outlet. An impeller having two blades which end offset by 180° with respect to each other in each case on the impeller extends in the assembled state through the drawn opening 71 facing an axial inlet. An exemplary impeller is shown in FIG. 7c. Correspondingly to the blading of the impeller, the tongues 67 and 67 respectively are arranged such that they are offset to one another by 180°. When a tongue 66 is swept over by a blade 63, the oppositely disposed tongue 67 is simultaneously swept over by the corresponding blade 64. The two flow paths 68 and 69 respectively are created in this manner. A particularly gentle blood conveying and smooth running is given by means of a double spiral chamber. Analogously to the double spiral chamber shown here, three-fold or N-fold spiral chambers can likewise be used whose tongues preferably have an offset of approximately 120° or approximately 360°/N from one another and the different flow paths combine at least toward the outlet. The impeller then preferably has a corresponding number of blades.

It must be pointed out at this point that although only cylindrical guide bodies and cylindrical impellers were shown in the present embodiments, in principle frusto-conical jacket-like impellers and frusto-conical guide bodies with hollow spaces are also possible. It must, however, be noted in this respect that the support of the impeller on the guide body is formed by a hydrodynamic bearing which is optionally also present by the radial bounding of the blading and the inner wall of a tube into which both the guide body and the impeller project.

Further variants of the invention result in an obvious manner for the skilled person and are likewise covered by enclosed claims.

In contrast to blood pumps in accordance with the prior art in which the stator is arranged radially inside the rotor, the geometrical conditions in a pump in accordance with the present invention are more favorable since both the housing and the rotor can be designed with small construction and lower mass. It is possible for this purpose that the axial tubular inlet has an unchanging cross-section, i.e. that the shape of the cross-section is uniform (for example round) and also that the inner cross-sectional surface of this inlet has an unchanging cross-section with respect to shape and cross-sectional area along the blood flow from the start of the hub (that is, for example, with reference to FIG. 1, starting at the tip of the guide body 8 up to the transition to the tangential chamber).

It must moreover be stated that the inner surface of the rotor is cylindrical and/or the outer surface of the rotor is cylindrical. A helix for blood conveying is then attached on the outer cylinder surface.

In this respect, the inlet is preferably provided in that region in which it radially surrounds the helix with an unchanging cross-section (i.e. for example with an unchanging inner pipe diameter).

Optionally, an abrupt cross-section expansion is present from the inlet toward the tangential chamber, with the helix being radially encompassed in the region of this transition. This means that both the inlet having the unchanging cross-sectional area and the tangential chamber adjoining it each radially surround the helix attached to the outer surface of the rotor.

It must moreover be emphasized that the axial seat or the axial positioning of the rotor with respect to the guide body takes place solely by the magnetic radial support (optionally supplemented by axial hydrodynamic bearings). This means that it is not necessary to provide wedge surfaces or conical surfaces which act against an axial displacement of the rotor on a pressure exerted by the fluid or on a conveying pressure of the helix.

The enveloping surface of the helix/blading of the rotor also preferably has the form of a cylinder jacket. In that region in which the inlet with unchanging cross-section, which is interposed in front of the tangential chamber, surrounds the rotor, the outer surface of the rotor or the enveloping surface of the helix/blading can/should have a cylindrical shape.

There can be supplements to/variations on these features, for example such that in exceptional cases additional magnetic bearings are provided for the axial fixing.

The invention claimed is:

1. A blood pump comprising
an axial tubular inlet having a cylindrical cross-section;
a tangential chamber adjoining the axial inlet and having a substantially radially directed outlet;
an axial guide body connected to at least one of the inlet or the tangential chamber;
an impeller supported on the guide body and having an inner surface facing the guide body and an outer surface;
blading arranged on the outer surface of the impeller, wherein at least a portion of the blading is in the cylindrical cross-section; and
a motor which includes a stator associated with the guide body and a rotor associated with the impeller, the stator comprising a coil configured to transmit force onto the rotor,
wherein a part region of the guide body includes the coil and projects from the tangential chamber into the cylindrical cross-section of the inlet, wherein a section of the coil is in the cylindrical cross-section of the axial tubular inlet and the impeller is supported by a hydrodynamic radial bearing in the radial direction.

2. A blood pump in accordance with claim 1, wherein the impeller is supported in the radial direction only by a hydrodynamic radial bearing formed between the inner surface of the impeller and the guide body outer surface.

3. A blood pump in accordance with claim 1, wherein the stator is arranged in a hollow space of the guide body.

4. A blood pump in accordance with claim 1, wherein the guide body is connected to a wall of the tangential chamber.

5. A blood pump in accordance with claim 1, wherein the coil includes windings and a ferrite core.

6. A blood pump in accordance with claim 1, wherein the impeller is made in cylinder jacket form in the part section.

7. A blood pump in accordance with claim 1, wherein the impeller includes a hollow space and the rotor is arranged in the hollow space.

8. A blood pump in accordance with claim 1, wherein the rotor includes at least one alternatingly magnetized segmented permanent magnet ring.

9. A blood pump in accordance with claim 8, wherein the permanent magnet ring is present as a one-piece ring magnet or is composed of respective individually magnetized part segments.

10. A blood pump in accordance with claim 1, wherein the impeller is arranged such that the blading is arranged both in the tangential chamber and in the inlet.

11. A blood pump in accordance with claim 10, wherein the blading includes a helix arranged on the outer surface.

12. A blood pump in accordance with claim 1, wherein at least one of: the inner surface of the impeller is a cylindrical inner surface, or the outer surface of the impeller is a cylindrical running surface.

13. A blood pump in accordance with claim 1, wherein the hydrodynamic radial bearing is formed by cut-outs on at least one of: the guide body outer surface or the inner surface of the impeller.

14. A blood pump in accordance with claim 1, wherein the hydrodynamic radial bearing includes two or more pairs of inner surface sections of the impeller and respective guide body outer surface sections corresponding thereto.

15. A blood pump in accordance with claim 1, wherein the impeller and the guide body are designed such that at least one of: the impeller is axially supported in an axial direction by the correspondingly configured motor, or the impeller is axially supported by permanent magnet systems not belonging to the motor.

16. A blood pump in accordance with claim 1, wherein the axial tubular inlet is not formed in one part with the tangential chamber.

17. A blood pump in accordance with claim 1, wherein the outlet is offset by an angle of more than 30° with respect to the inlet.

18. A blood pump in accordance with claim 1, wherein at least a majority of the blading is in the cylindrical cross-section.

19. A blood pump in accordance with claim 1, wherein the section of the coil in the cylindrical cross-section includes all of the coil.

20. A blood pump in accordance with claim 1, wherein the tangential chamber joins the axial inlet at an angle of 90°.

21. A blood pump in accordance with claim 1, wherein at least 40 percent of the part region of the guide body is in the cylindrical cross-section.

22. A blood pump comprising:
an axially tubular inlet having a cylinder-shaped elongated section;
a tangential chamber adjoining the axial inlet and having a substantially radial outlet;
an axial guide body connected to at least one of the axially tubular inlet or the tangential chamber, wherein the axial guide body projects into the axially tubular inlet;
an impeller supported on the guide body and having an inner surface facing the guide body and an outer surface; and
a motor which includes a coil associated with the guide body and a rotor associated with the impeller, wherein the coil is configured to transmit force onto the rotor and cause blading on the impeller to rotate inside of the cylinder-shaped elongated section of the inlet, and wherein a section of the coil is located in the cylinder-shaped elongated section of the inlet.

23. A blood pump comprising:

an axially tubular inlet with an elongated section of a substantially constant diameter;

a tangential chamber adjoining the axial inlet and having a substantially radial outlet;

an axial guide body connected to at least one of the tube or the tangential chamber, wherein a portion of the axial guide body is in the elongated section of the axial inlet having the substantially constant diameter;

an impeller supported on the guide body and having an inner surface facing the guide body and an outer surface; and a motor which includes a coil associated with the guide body and a rotor associated with the impeller, wherein the coil is configured to cause blading on the impeller to rotate inside of the elongated section of the axial inlet having the substantially constant diameter, wherein a section of the coil is located is in the elongated section of the axial inlet having the substantially constant diameter, wherein the guide body includes a cylindrical guide body outer surface in the part region and the impeller is made in cylinder sleeve form in the part section.

* * * * *